United States Patent
Blacker et al.

(10) Patent No.: US 6,450,163 B1
(45) Date of Patent: *Sep. 17, 2002

(54) BREATH ACTUATED NEBULIZER WITH VALVE ASSEMBLY HAVING A RELIEF PISTON

(75) Inventors: Rick Blacker, London (CA); Alex M. W. Verdun, London (CA)

(73) Assignee: Trudell Medical International (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/447,016

(22) Filed: Nov. 22, 1999

Related U.S. Application Data

(63) Continuation of application No. 08/921,176, filed on Aug. 29, 1997.

(51) Int. Cl.⁷ ............................ A61M 11/00; B05B 1/26
(52) U.S. Cl. ............................ 128/200.18; 128/200.14; 128/200.21
(58) Field of Search ................. 128/200.18, 200.14, 128/200.21, 200.16, 200.19, 200.23

(56) References Cited

U.S. PATENT DOCUMENTS

| | | |
|---|---|---|
| 2,535,844 A | 12/1950 | Emerson |
| 3,467,092 A | 9/1969 | Bird et al. |
| 3,580,249 A | 5/1971 | Takaoka |
| 3,584,621 A | 6/1971 | Bird et al. |
| 3,630,196 A | 12/1971 | Bird et al. |
| 3,658,059 A | 4/1972 | Steil |
| 3,826,255 A | 7/1974 | Havstad et al. |
| 3,838,686 A | 10/1974 | Szekely |
| 3,874,379 A | 4/1975 | Enfield et al. |
| 3,990,442 A | 11/1976 | Patneau |
| 4,116,387 A | 9/1978 | Kremer, Jr. et al. |
| 4,251,033 A | 2/1981 | Rich et al. |
| 4,268,460 A | 5/1981 | Boiarski et al. |
| 4,333,450 A | 6/1982 | Lester |
| 4,588,129 A | 5/1986 | Shanks |
| 4,620,670 A | 11/1986 | Hughes |
| 4,674,491 A | 6/1987 | Brugger et al. |
| 4,746,067 A | 5/1988 | Svoboda |
| 4,792,097 A | 12/1988 | Kremer, Jr. et al. |
| 5,020,530 A | 6/1991 | Miller |
| 5,054,477 A | 10/1991 | Terada et al. |
| 5,054,478 A | 10/1991 | Grychowski |
| 5,086,765 A | 2/1992 | Levine |
| 5,165,392 A | 11/1992 | Small |
| 5,277,175 A | 1/1994 | Riggs et al. |
| 5,280,784 A | 1/1994 | Köhler |
| 5,301,662 A | 4/1994 | Bagwell et al. |

(List continued on next page.)

FOREIGN PATENT DOCUMENTS

| | | |
|---|---|---|
| EP | 0587380 | 3/1994 |
| EP | 0 711 609 A3 | 10/1996 |
| FR | 1 070 292 | 7/1954 |
| FR | 93306974.2 | 3/1993 |
| GB | 675524 | 7/1952 |

*Primary Examiner*—John G. Weiss
*Assistant Examiner*—Darwin Erezo
(74) *Attorney, Agent, or Firm*—Brinks Hofer Gilson & Lione

(57) ABSTRACT

A breath actuated nebulizer for efficiently and reliably delivering aerosolized liquid to an inhaling patient is disclosed. The nebulizer includes a valve assembly having an actuator piston for quickly responding to an inhalation and beginning the nebulization process, and a relief piston to lower the inhalation effort required of the inhaling patient. Also provided is a method of providing breath actuated nebulization including the steps of moving an actuator piston connected to a diverter so that the diverter reaches a nebulizing position during an initial period of inhalation, and moving a relief valve to allow a greater flow of air, and thereby reduce inhalation effort, after the initial period of inhalation.

21 Claims, 6 Drawing Sheets

U.S. PATENT DOCUMENTS

| | | |
|---|---|---|
| 5,301,663 A | 4/1994 | Small, Jr. |
| 5,312,046 A | 5/1994 | Knoch et al. |
| 5,318,015 A | 6/1994 | Mansson et al. |
| 5,398,714 A | 3/1995 | Price |
| 5,458,136 A | 10/1995 | Jaser et al. |
| 5,479,920 A | 1/1996 | Piper et al. |
| 5,505,193 A | 4/1996 | Ballini et al. |
| 5,511,538 A | 4/1996 | Haber et al. |
| 5,515,842 A | 5/1996 | Ramseyer et al. |
| 5,520,166 A | 5/1996 | Ritson et al. |
| 5,533,497 A | 7/1996 | Ryder |
| 5,533,501 A | 7/1996 | Denyer |
| 5,570,682 A | 11/1996 | Johnson |
| 5,584,285 A | 12/1996 | Saltes et al. |
| 5,613,489 A | 3/1997 | Miller et al. |
| 5,617,844 A | 4/1997 | King |
| 5,622,162 A | 4/1997 | Johansson et al. |
| 5,630,409 A | 5/1997 | Bono et al. |
| 5,687,912 A | 11/1997 | Denyer |
| 5,803,078 A | 9/1998 | Brauner |
| 5,823,179 A | 10/1998 | Grychowski et al. |
| 5,875,774 A | 3/1999 | Clementi et al. |
| 6,044,841 A | 4/2000 | Verdun et al. |
| 6,116,233 A | 9/2000 | Denyer et al. |
| 6,129,080 A * | 10/2000 | Pitcher et al. .......... 128/200.21 |
| 6,131,568 A * | 10/2000 | Denyer et al. .......... 128/200.21 |
| 6,223,745 B1 * | 5/2001 | Hammarlund et al. . 128/200.18 |
| 6,237,589 B1 | 5/2001 | Denyer et al. |

* cited by examiner

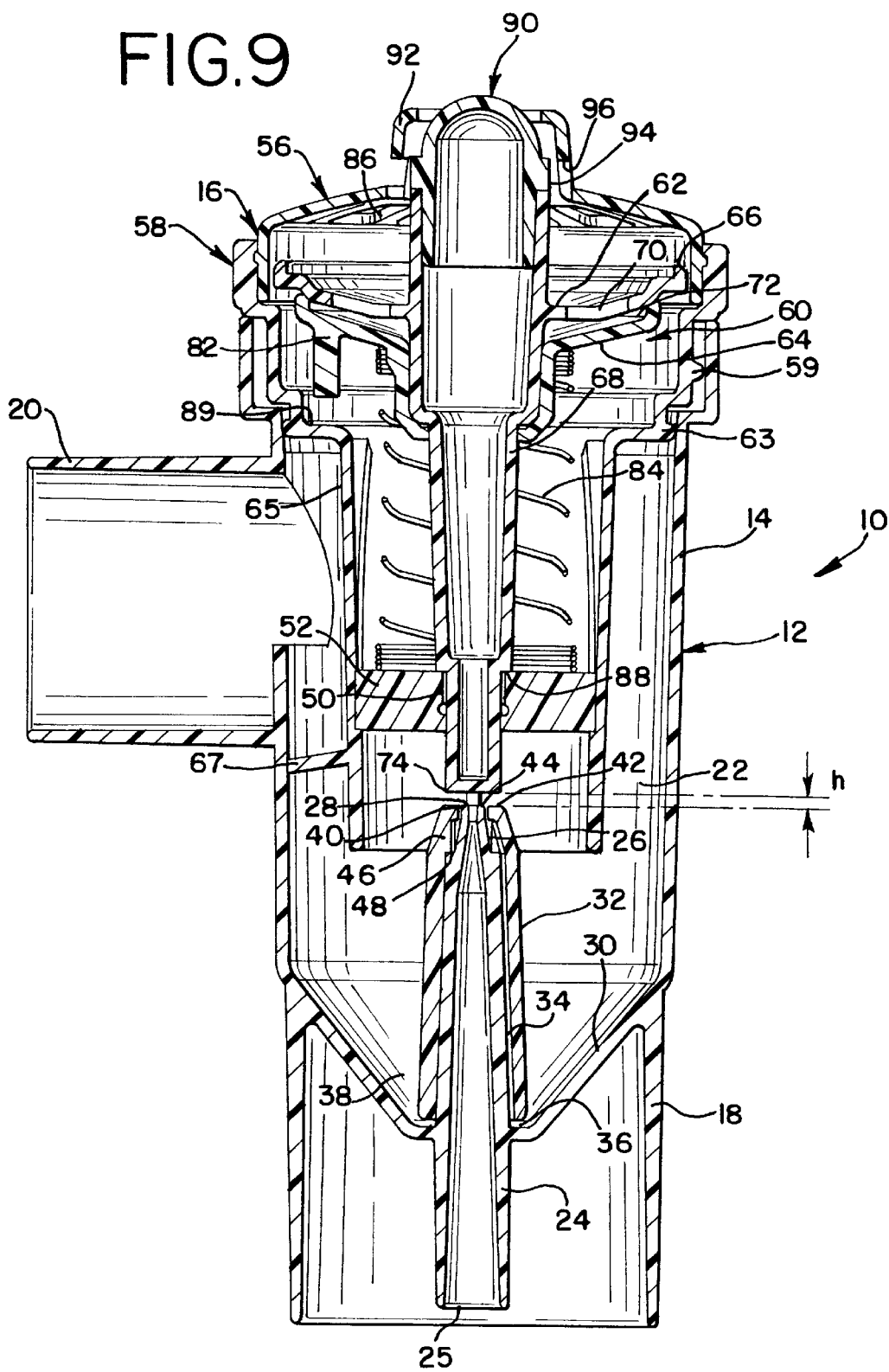

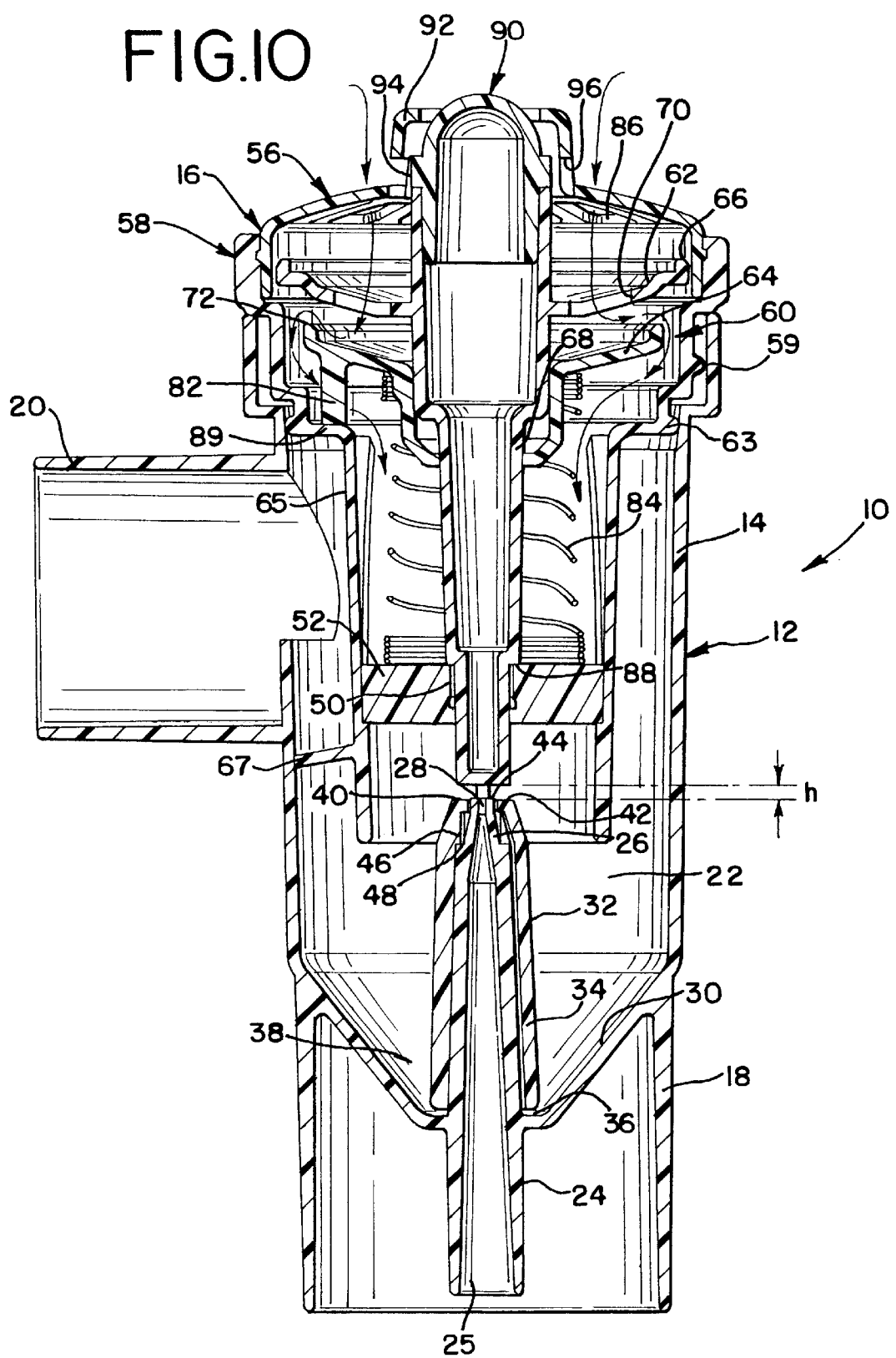

BREATH ACTUATED NEBULIZER WITH VALVE ASSEMBLY HAVING A RELIEF PISTON

This Application is a continuation of U.S. application Ser. No. 08/921,176, filed Aug. 29, 1997.

BACKGROUND OF THE INVENTION

The present invention relates to a method and apparatus for delivering an aerosol, nebulized liquid, solid medicine or a vapor to a patient's respiratory tract. More particularly, the present invention relates to a breath actuated nebulizer with reduced resistance to a patient's inhalation.

Medical nebulizers that generate a fine spray or nebula of a liquid medicine for inhalation by a patient are well-known devices commonly used for the treatment of certain conditions and diseases. Nebulizers have applications for conscious, spontaneously-breathing patients and for controlled, ventilated patients.

In some nebulizers, a gas and a liquid are mixed together and directed against a baffle. As a result, the liquid is aerosolized, that is, the liquid is caused to form small particles that are suspended in the air. This aerosol of the liquid can then be inhaled into a patient's respiratory tract. One way to mix the gas and liquid together in a nebulizer is to pass a quickly moving gas over a liquid orifice tip of a tube. A negative pressure created by the flow of pressurized gas is a factor that contributes to drawing liquid out of the liquid orifice into the stream of gas and nebulizing it.

Important considerations in the design of a nebulizer are the timing and dosage regulation of the aerosolized medication. In some nebulizer designs, a continuous stream of pressurized gas entrains the liquid against the baffle to constantly generate aerosol particles until the liquid in a reservoir is depleted. Continuous nebulization may result in a waste of aerosol during a patient's exhalation or during a delay between inhalation and exhalation. The amount of wasted aerosol may be difficult to quantify and some medication may be lost to condensation on the nebulizer or mouthpiece during periods of non-inhalation. Nebulizers implementing a timed or non-continuous nebulization may adversely affect particle size and density as the nebulization is turned on and off.

Effective and economical nebulizer therapy includes the ability to quickly generate a large amount of aerosol within a predetermined particle size range. An effective nebulizer preferably provides these features synchronously with the inhalation of the patient. Additionally, it is desirable that a nebulizer have adequate sensitivity to quickly respond to an inhalation while not adversely restricting the patient's inhalation. Further, an indication that the nebulizer is responding to the patient's inhalation would be useful.

Accordingly, there is a need for an improved nebulizer having these characteristics.

SUMMARY OF THE INVENTION

According to a first aspect of the invention, a nebulizer is provided having a housing with a chamber for holding an aerosol. An air outlet is connected to the chamber permitting the aerosol to be withdrawn from the chamber. A liquid orifice communicates with the chamber. A pressurized gas inlet is positioned adjacent the liquid orifice and is also in communication with the chamber. A diverter movably positioned in the chamber and relative to the air inlet and liquid orifice is designed to divert pressurized gas from the inlet and over the liquid orifice when the diverter is in a nebulizing position. A valve assembly comprising an actuator piston and a relief piston are positioned in the chamber. The actuator piston is connected to the diverter and responsive to inhalation through the air outlet so that the diverter quickly moves into the nebulizing position during the beginning of an inhalation. The relief piston is responsive to additional negative pressure in the chamber after the initial period of inhalation and is movable to allow increased air flow into the chamber so that the effort necessary for a patient inhaling through the air outlet is maintained in a desired range. In one preferred embodiment, a nebulization indicator attached to the actuator piston provides a visual cue that nebulization has begun.

According to another aspect of the invention, a method of providing a patient with an aerosol flow of medicine includes the steps of providing a nebulizer having an outlet for delivering of the aerosol to the patient, a chamber, an actuator piston having a diverter mounted in the chamber, and a relief piston connected to the actuator piston and inhaling air from the chamber through the outlet. The actuator piston and diverter move from an initial position to a predetermined distance from a pressurized gas inlet in the chamber. The diverter diverts pressurized gas injected into the chamber and creates a negative pressure over a liquid outlet. The negative pressure draws medication through the liquid outlet and begins nebulization. The relief valve is then opened to permit greater air flow through the chamber after the diverter has moved to the predetermined distance from the pressurized gas inlet and nebulization has begun.

BRIEF DESCRIPTION OF THE DRAWINGS

FIG. 9 is a cross-sectional view of the nebulizer of FIG. 1 showing the position of the pistons and diverter during an initial period of an inhalation.

FIG. 10 is a cross-sectional view of the nebulizer of FIG. 1 showing the relief valve in an open position after the initial period of an inhalation.

DETAILED DESCRIPTION OF THE PRESENTLY PREFERRED EMBODIMENTS

Figure 1:
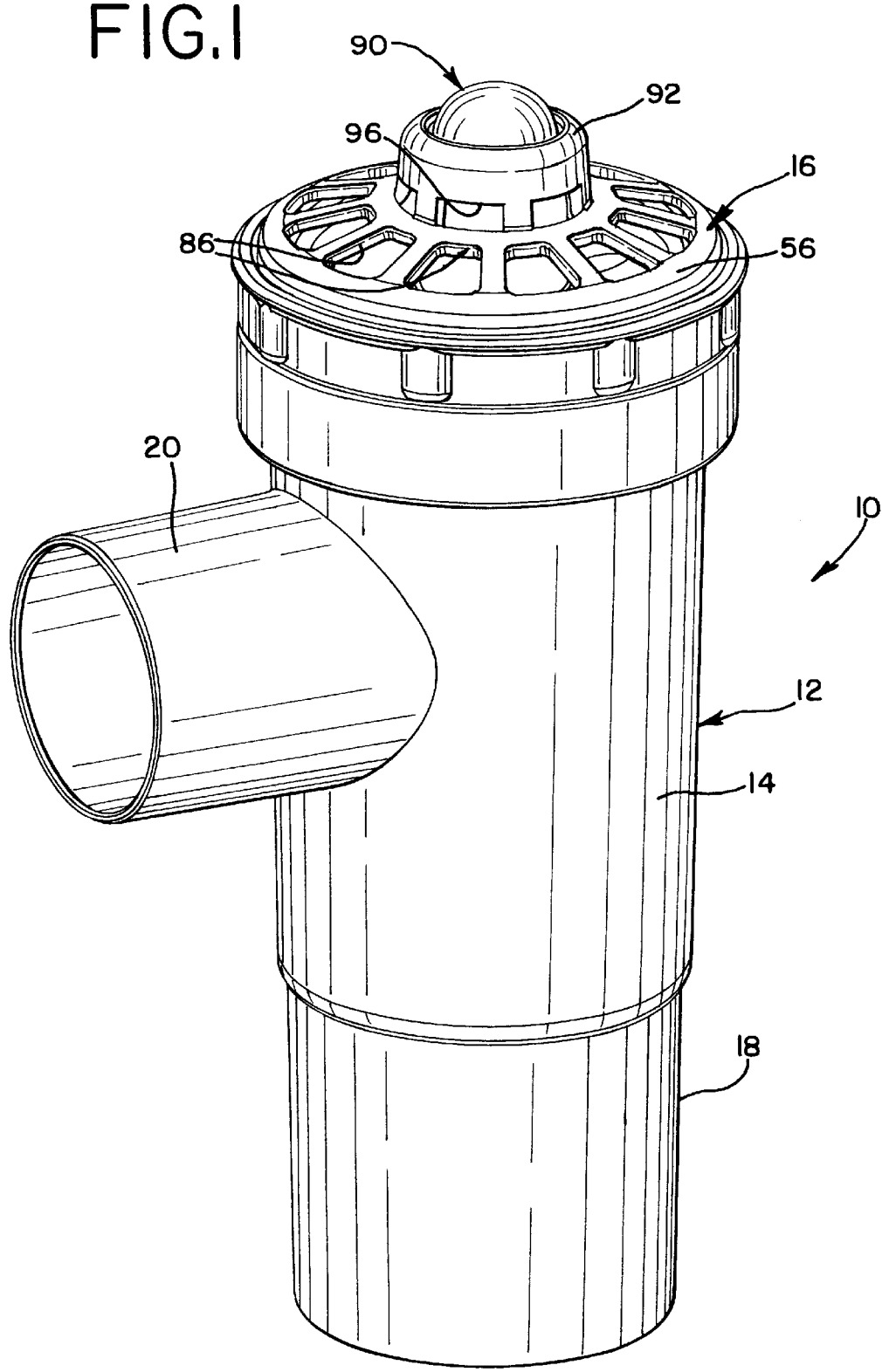
FIG. 1 is a perspective view of a preferred embodiment of the nebulizer according to the present invention.
Figure 2:
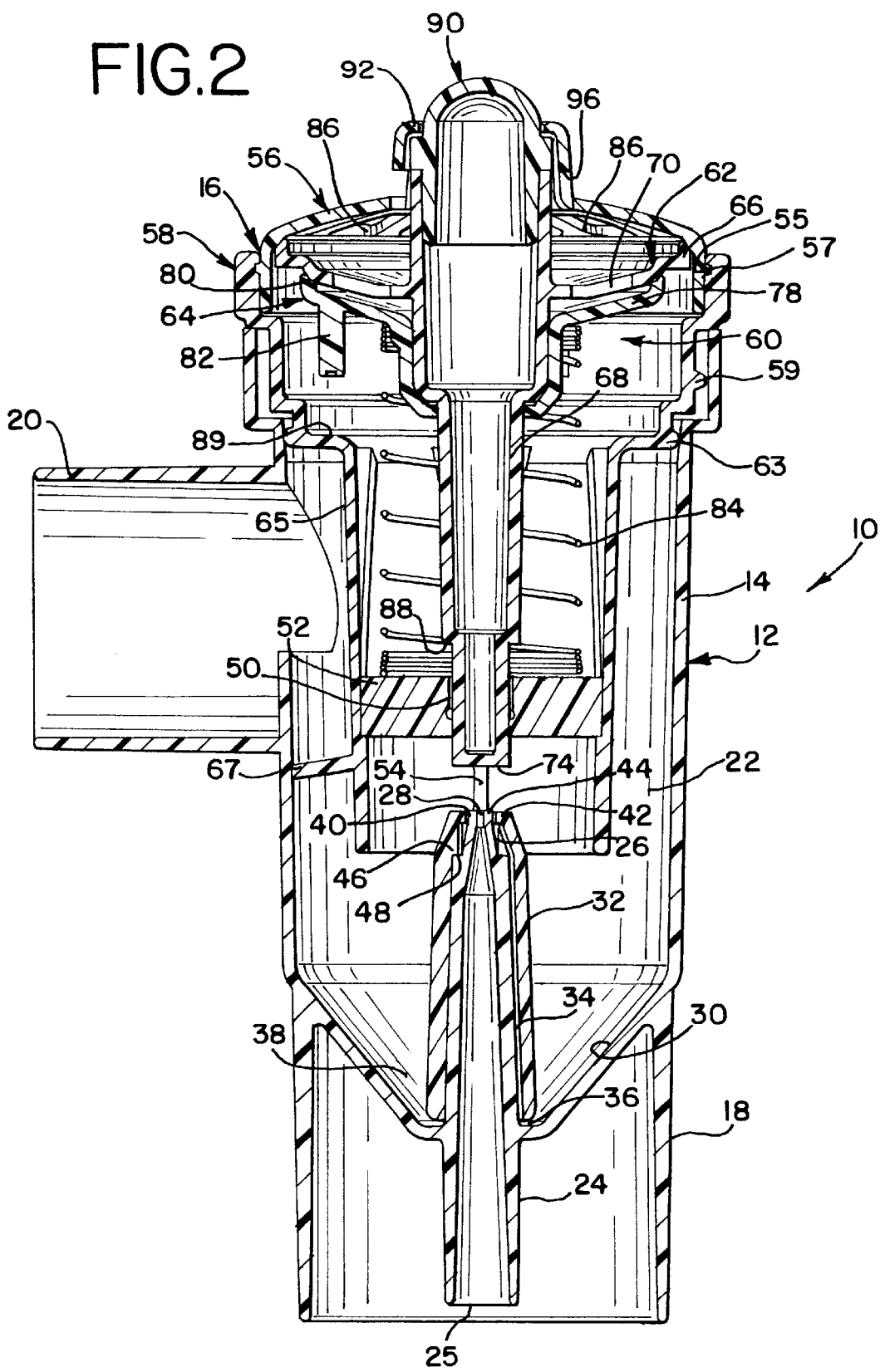
FIG. 2 is a cross-sectional view of the nebulizer of FIG. 1.

A preferred embodiment of a nebulizer 10 is shown in FIGS. 1 and 2. The nebulizer 10 includes housing 12 having a cylindrical body 14, a top portion 16, and a bottom portion 18. An air outlet 20 extends from the cylindrical body 14 of the housing 12. The air outlet communicates with air in the chamber 22 defined by the inside of the housing 12. The component parts of the housing 12 may be formed of separate, multiple pieces of material that are connected together by welding, adhesives, etc., or more preferably, some of the component parts may be formed together with a single piece of material formed by an injection molding process. The housing 12 may be constructed from a plastic material such as polycarbonate or a polycarbonate blend. As will be recognized by those of ordinary skill in the art, any of a number of types of plastic may be used to construct these parts of the nebulizer.

As shown in FIG. 2, a pressurized gas inlet 24 extends into the chamber 22 through the bottom portion 18 of the housing 12. The opening 25 of the pressurized gas inlet 24 is designed to connect with a standard vinyl gas hose (not shown). Inside the chamber 22, the pressurized gas inlet 24 forms a nozzle 26 that tapers down to a pressurized gas orifice 28 having a predetermined diameter. Preferably, the gas inlet 24 is coaxial with the cylindrical body and extends through the bottom wall 30 of the chamber 22.

Figure 3:
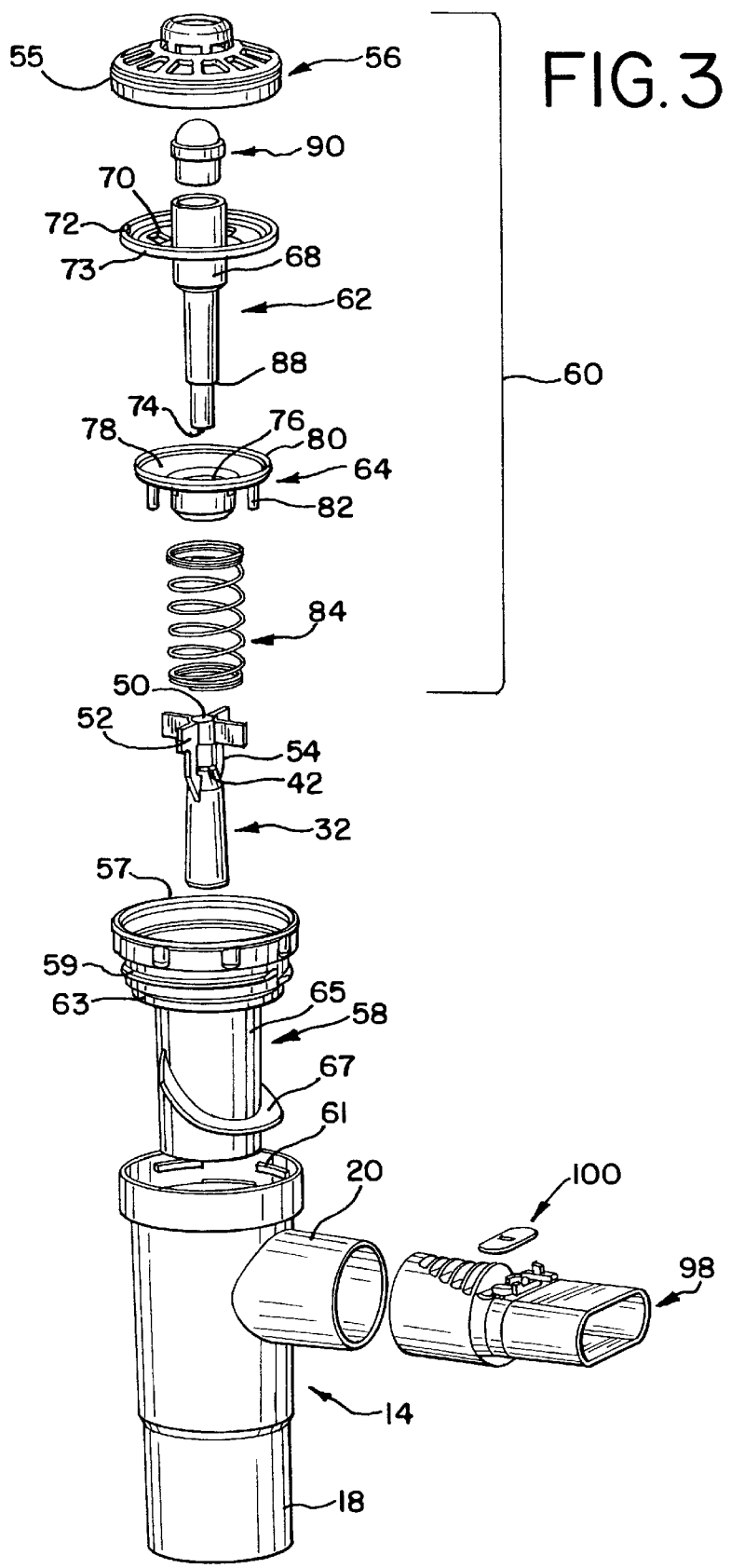
FIG. 3 is an exploded view of the nebulizer of FIG. 1.
Figure 4:
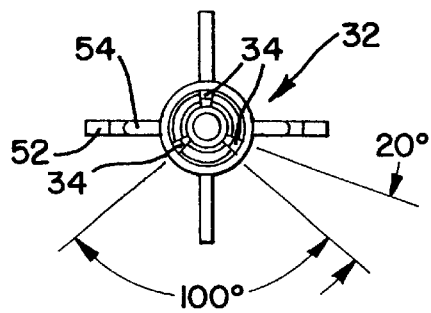
FIG. 4 is a bottom view of a preferred nozzle cover for use in the nebulizer of FIG. 1.
Figure 5:
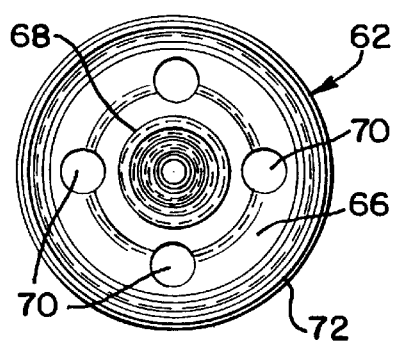
FIG. 5 is a top plan view of a preferred actuator piston used in the nebulizer of FIG. 1.

FIGS. 2 and 3 best show that a nozzle cover 32 removably fits over the nozzle 26. The nozzle cover 32 is preferably a tapered tubular member having openings at either end, The nozzle cover 32 slides over the nozzle 26 of the pressurized gas inlet 24 to form at least one passageway 34 between an opening 36 located near the bottom wall 30 and an annular orifice 40. The annular orifice 40 is defined by the gap between the inner diameter of the tip 42 of the nozzle cover 32 and the outer diameter of the tip 44 of the nozzle 26. To maintain the proper size of the opening 36 and position of the nozzle cover 32 over the nozzle 26, a retaining tab 46 on the inside of the nozzle cover 32 is designed to cooperate with a ledge 48 formed near the tip 44 of the nozzle 26.

The lower portion of the chamber 22 is preferably used as a reservoir 38. The reservoir 38 at the bottom of the chamber 22 holds a fluid for nebulizing, such as a solution containing a medication. In the embodiment shown in FIG. 2, the bottom wall 30 slopes down to the nozzle 26 so that gravity urges the fluid in the reservoir 38 toward the opening 36. In one embodiment, the cylindrical body 14 and bottom portion 18 of the housing are constructed from a transparent plastic to allow medical personnel to monitor medication levels in the nebulizer 10. The passageway 34 guides fluid from the reservoir 38 through the opening 36 to the annular orifice 40.

Preferably, a plurality of passageways connect the annular orifice with the fluid in the reservoir. Each passageway is formed by a slot on the inside of the nozzle cover 32. The characteristics of the aerosol generated in the nebulizer, in addition to the mass output of the nebulizer, may be varied by varying the size and number of passageways. As illustrated in FIG. 4, in one preferred embodiment there are three passageways 34 each having a circumferential width of approximately 20° and spaced evenly around the nozzle cover 32. The radial width of each passageway 34 is defined by the depth of the slot in the nozzle cover 32. In the embodiment shown in FIG. 4, the radial width of the passageways is a constant 0.02 inches from the opening 36 by the bottom wall 30 to the annular orifice 40. Other passageway dimensions and arrangements may be implemented to achieve the desired aerosol size and density during nebulization.

The pressurized gas orifice 28 is preferably circular in shape and concentrically aligned with the annular orifice 40 connected to the liquid passageways 34. In one preferred embodiment, the diameter of the pressurized gas orifice 28 is approximately 0.018 inches and the annular orifice has an inner diameter of 0.080 inches and an outer diameter of 0.096 inches. The tip 42 of the nozzle cover and tip 44 of the nozzle are preferably flat surfaces. Preferably, the pressurized gas orifice is positioned flush with the plane of the annular liquid orifice or extends up to 0.010 inches above the plane of the annular liquid orifice 40. In other preferred embodiments, the tips of the nozzle cover and nozzle 42, 44 may have non-planer shapes. Additionally, although the tip of the nozzle 44 may extend more than 0.010 inches above the plane of the tip of the nozzle cover 42, it is most preferred that the pressurized gas orifice not go below the liquid annular orifice. The relative heights of the tips 42, 44 may be adjusted to achieve the desired nebulization characteristics.

The nozzle cover 32 also preferably includes a diverter guide 50 and spring support members 52. The diverter guide 50 has a hollow passageway coaxially aligned with the pressurized gas orifice 28 and annular orifice 40. The diverter guide 50 is formed by the opening in the center of the spring support members 52 attached to the top portion of the nozzle cover 32 by integrally formed arms 54.

On the opposite end of the nebulizer housing 12, the top portion 16 is removably attachable to the cylindrical body 14. The top portion 16 includes a retainer lid 56 detachably connected to a chimney section 58. An annular rib 55 on the outside of the retainer lid 56 forms a removable snap-fit connection with a receiving groove 57 on the inside of the chimney section 58. The chimney section 58 removably attaches to the inside of cylindrical body 14, preferably with threads 59 designed to cooperate with a female threaded area 61 in the housing 12. A seal, which may be in the form of an integrally formed annular rib 63, protrudes from the chimney section 58 and prevents air or nebulized medication from entering or exiting the chamber 22 between the chimney section 58 and cylindrical body 14. A conical extension 65 of the chimney section 58 extends into the chamber 22 and down below the tip of the nozzle cover 32. The conical extension 65 and a secondary diverter 67, or baffle, on the exterior of the conical extension preferably act to remove undesirable larger particles from nebulized liquid in the chamber.

The retainer lid 56 and chimney 58 contain a valve assembly 60 for permitting controlled amounts of ambient air to enter into the chamber 22 during a patient's inhalation. As best shown in FIGS. 2–8, the valve assembly 60 includes an actuator piston 62 and a relief piston 64. The actuator piston 62 has a circumferential flange 66 attached to a coaxial body 68 extending down into the chimney 58. The circumferential flange 66 of the actuator piston 62 covers the ambient air inlet and defines at least one, and preferably a plurality of, vents or openings 70 for permitting ambient air to pass through. The upturned rim 72 of the circumferential flange 66 preferably forms a seal with the inside of the retainer lid 56. The seal formed by the rim 72 of the flange and the retainer lid 56, in cooperation with the relief valve 64, prevents air from escaping the chamber 22 when a patient exhales into the air outlet 20. In order to permit movement of the actuator piston within the inner wall of the retainer lid 56, there is preferably a small clearance between the outer circumference 73 of the flange 66 and the inner wall of the retainer lid 56. Because the response time of the actuator piston 62 is lengthened by increasing the clearance, the clearance is preferably kept to a minimum so that the breath actuation action of the nebulizer maintains a fast response time.

The coaxial body 68 of the actuator piston 62 extends into the chimney 65 along the longitudinal axis of the nebulizer 10. The closed end of the coaxial body 68 defines a diverter 74 for diverting the flow of pressurized gas emerging from the pressurized gas orifice 28. Preferably, the portion of the coaxial body adjacent to the diverter 74 is slideably positioned in the diverter guide 50 attached to the nozzle cover 32. In a preferred embodiment, the diverter 74 has a flat surface having a predetermined area. The surface is also preferably aligned parallel to the surface of the tip of the nozzle 44 and perpendicular to the direction of flow of pressurized gas through the pressurized gas orifice 28. One suitable diverter 74 has a circular area with a diameter of approximately 0.180 inches.

Figure 7:
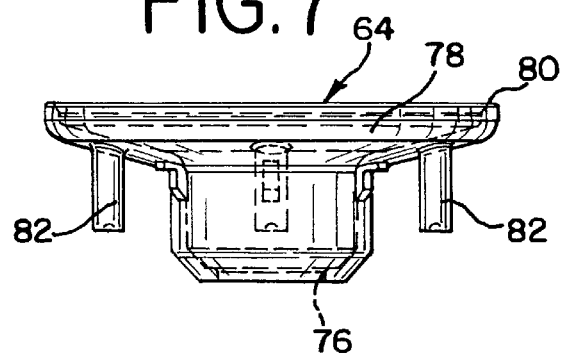
FIG. 7 is a side elevational view a preferred relief piston for use in the nebulizer of FIG. 1.
Figure 6:
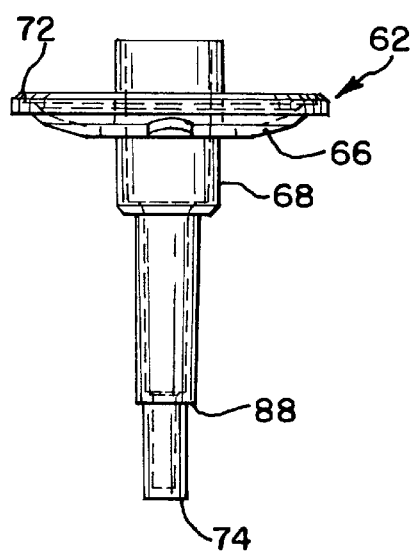
FIG. 6 is a side elevational view of the actuator piston of FIG. 5.
Figure 8:
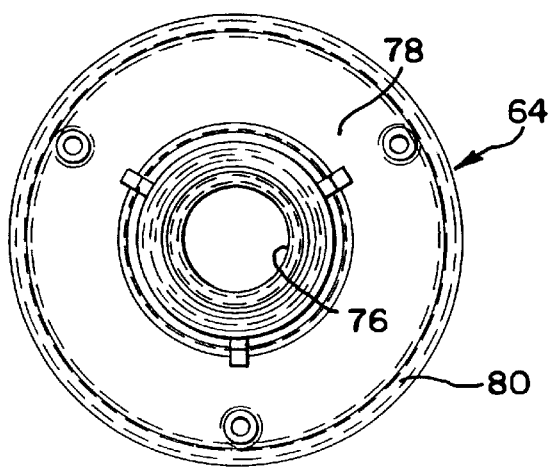
FIG. 8 is a top plan view of the preferred relief valve of FIG. 7.

The relief piston 64 is coaxially and slideably mounted on the coaxial body 68 of the actuator piston 62. As best shown in FIGS. 7 and 8, the relief piston 64 has a hollow bore 76 sized to slideably fit along a portion of the coaxial body 68 of the actuator piston 62. The relief piston 64 also includes a circumferential flange 78 having a diameter sufficient to cover openings 70 in the flange 66 of the actuator piston 62. As explained in greater detail below, the openings 70 in the flange 66 allow ambient air to be drawn into the chamber 22 from outside the nebulizer 10 and out through the air outlet 20 during inhalation. The circumferential flange of the relief valve is preferably bowl-shaped so that the outer edge 80 of the flange 78 contacts and seals against the circumferential flange 66 of the actuator piston when the relief piston 64 is closed. Preferably, the relief piston 64 has a circumferential flange 78 having a smaller diameter than the circumferential flange 66 of the actuator piston 62. The relief piston 64 also includes a plurality of travel limiters 82 extending from the bottom portion of the relief piston 64 at a predetermined radial distance from the bore 76.

A biasing member, such as a spring 84, frictionally fits around the exterior of the relief piston 64 adjacent to the bore 76 and rests against the spring support members 52 attached to the nozzle cover 32. The biasing member is designed to have a resistance to motion that is sufficiently strong enough to hold the valve assembly closed until inhalation begins, yet responsive enough to quickly react to negative pressures generated by inhalation. Preferably, a precision spring having a constant spring rate is used as the biasing member. A suitable spring for use in a presently preferred embodiment has a spring rate of 0.6 gm/mm.

Referring now to FIGS. 2, 9, and 10, the operation of the presently preferred embodiment of a nebulizer 10 will be explained. FIG. 2 illustrates the nebulizer with the actuator and relief pistons 62, 64 fully closed. The nebulizer maintains this configuration during exhalation. Although the patient is exhaling, pressurized gas is continuously entering the chamber 22 via the pressurized gas orifice 28. In this configuration, the diverter 74 is at a great enough distance from the tip of the nozzle 44 such that the pressurized gas does not initiate nebulization The force of the spring 84 against the spring support member 52 on one end and against the relief piston 64 on the other end holds the relief piston 64 and actuator piston 62 closed so that no air escapes from the chamber 22 through the retainer lid openings 86. When a patient begins inhaling through the air outlet 20, the force of the inhalation lowers the pressure in the chamber 22 and pulls the actuator piston 62 down. More specifically, when the rate of air flow through the air outlet 20 exceeds the rate of flow of pressurized gas constantly supplied to the nebulizer 10, a negative pressure is created in the chamber 22.

Referring to FIG. 9, when the rate of airflow out the air outlet exceeds the pressurized gas flow and the negative pressure on the valve assembly exceeds the force of the spring, the actuator piston 62 moves downward, the spring 84 compresses and the diverter 74 on the end of the coaxial body 68 moves to a predetermined distance ‘h’ from the orifice 28 in the nozzle 26 appropriate for nebulization. Preferably, a retaining ridge 88 around the coaxial body 68 of the actuator piston 62 has a greater diameter than the diameter of the diverter guide 50 so that the diverter 74 stops at the desired distance ‘h’ from the tip of the nozzle 44. During this initial stage of inhalation, the force of the spring 84 against the relief piston 64 holds the relief piston closed against the actuator piston 62. Thus, no air flows through the openings 70 in the circumferential flange 66 of the actuator piston 62 allowing the actuator piston to respond quickly to begin nebulization at the start of an inhalation.

As noted above, nebulization of a fluid in the reservoir 38 begins as soon as the diverter 74 reaches the appropriate distance ‘h’ from the tip 44 of the nozzle where the pressurized gas orifice 28 is located. Preferably ‘h’ is 0.045 inches. The pressurized gas, which may be oxygen, continuously flowing from the pressurized gas orifice is now deflected radially outward from the gas orifice in a 360° pattern by the deflector 74. The gas fans out over the annular orifice at a high velocity creating a low pressure zone over the annular orifice. The low pressure zone, along with a capillary effect, draws the liquid from the reservoir 38 through the passageways 34 and into the stream of pressurized gas.

The liquid is aerosolized and drawn out the air outlet 20 through a mouthpiece 98 (FIG. 3) and into the patient’s respiratory system. To improve the performance of the nebulizer in eliminating non-optimally sized particles, the conical extension 65 of the chimney extends around and below the plane of the tip 44 of the nozzle. The conical extension acts to intercept oversized particles entrained in the gas flow directed by the diverter 74. These particles condense on the inside of the conical extension 67 and fall back into the reservoir. The secondary diverter 67 also helps to decrease oversized particles in the air inhaled through the air outlet 20. The secondary diverter 67 collects additional oversized particles and directs the ambient air down into the chamber to take a more circuitous route through the aerosol and chamber before it leaves the nebulizer. The flowpath within the chamber 22 insures that a significant amount of ambient air is entrained to limit the particle density and, accordingly, reduce the chances of particle growth through accidental particle collisions.

As best shown in FIG. 10, the relief piston 64 separates from the actuator piston 62 after the initial period of the patient’s inhalation. The decrease in pressure in the chamber 22 caused by the continuing inhalation of the patient puts a force on the relief piston 64 that overcomes the force of the spring 84 in the opposite direction. Ambient air from outside of the nebulizer 10 may now flow through the opening in the retainer lid 56 and through the previously covered openings in the flange 70 of the actuator piston 62. The air flow, shown by arrows in FIG. 10, moves down through the conical extension 65 of the chimney 58 into the chamber 22. The travel limiters 82 extending from the relief piston 64 rest against a ledge 89 formed in the chimney so that the ambient air path through the actuator piston 62 and around the perimeter of the relief piston is not cut off. When the patient finishes an inhalation, the relief piston 64 moves back up against the actuator piston 62 and the actuator piston 62 seals against the inside of the retainer lid 56 as shown in FIG. 2. During exhalation, relief valve 100 on the mouthpiece 98 operates to direct exhalation away from the nebulizer. Any of a number of commonly available relief valves may be used with the presently preferred embodiment.

An advantage of the presently preferred device and method is that a quick response time to a patient’s inhalation is achieved while also providing for reduced resistance to the inhalation. In order to minimize the response time, the nebulizer is designed to minimize the amount of air flow required to move the actuator and begin nebulization. The air flow through the air outlet needed to begin nebulization may be adjusted to the desired level by design of the clearance between the outer circumference of the actuator piston flange and the inner circumference of the retainer lid, the spring force on the relief piston, and the force of the pressurized gas against the diverter. Using a preferred embodiment of the nebulizer as set forth above, and assuming a pressurized gas flow rate of 8 liters per minute (l.p.m.) at 40 to 50 pounds per square inch (p.s.i.), the actuator piston will actuate and begin the nebulization process once the patient begins inhaling at a rate of approximately 16 to 17 l.p.m. (a negative pressure of approximately 0.5 cm to 1.0 cm water below ambient). The response of the actuator piston may be modified by changing the pressure of the pressurized gas introduced into the chamber. Alternatively, the nebulizer may be constructed having a different flange to retainer lid clearance, a different actuator piston diameter and/or a different spring strength.

Another feature of a preferred nebulizer is a nebulizing indicator, such as a flag 90, that is visible to indicate when the diverter 74 is in position to nebulize the liquid from the reservoir 38. As shown in FIGS. 2, 9, and 10, the flag 90 preferably frictionally fits into the open upper end of the actuator piston 62 so that it moves synchronously with the diverter 74 and the actuator piston 62. During exhalation (FIG. 2), the flag 90 rests against a housing 92 in the retainer lid 56. As soon as the diverter moves to a predetermined distance from the pressurized gas orifice 28 on the nozzle 26, a visible indicator 94 on the flag 90 is viewable through windows 96 in the housing 92. The visible indicator 94 may be a colored section contrasting with the color of the rest of the nebulizer 10. FIGS. 9 and 10 illustrate that the visible indicator portion 94 of the flag 90 becomes visible as soon as inhalation begins and remains visible as long as the diverter is in the predetermined position away from the pressurized gas orifice 28. The entire flag 90 may be constructed of a colored material that contrasts with the color of the rest of the nebulizer 10.

As shown in the attached figures and described above, an improved breath actuated nebulizer has been disclosed that is designed for fast-starting nebulization during an initial portion of an inhalation and that has a relief piston to decrease the effort with which a patient needs to inhale through the nebulizing device. Additionally, a nebulization indicator has been disclosed that permits simple visual verification of nebulization. Although the embodiment shown illustrates a diverter that moves toward the pressurized gas orifice, other components may be moved to create the required ratio of distance between the gas orifice, liquid orifice and diverter. For example, the gas or liquid orifices may be movable in response to inhalation while the diverter remains stationary. In another preferred embodiment, the biasing member that flexes in response to the patient's breathing may be designed to deactivate nebulization upon exhalation by moving the diverter and nozzle apart during exhalation and continuously nebulizing during all other times.

It is intended that the foregoing detailed description be regarded as illustrative rather than limiting, and that it be understood that the following claims, including all equivalents, are intended to define the scope of this invention.

We claim:

1. A breath actuated nebulizer for providing an aerosol to an inhaling patient, the nebulizer comprising:

a housing having a chamber for holding the aerosol;

an air outlet communicating with the chamber for permitting the aerosol to be withdrawn from the chamber;

an air outlet communication with the chamber for allowing a supply of air to enter the chamber;

a liquid outlet located in the chamber;

a pressurized gas outlet located in the chamber adjacent to the liquid outlet;

means for generating an aerosol in the chamber from the liquid outlet during an inhalation through the air outlet, the means for generating an aersol comprising a movable diverter; and means for reducing an inhalation effort of the inhaling patient in a desired range after an initial period of inhalation, wherein the means for reducing an inhalation effort is movable independently of the means for generating an aerosol and movable relative to the housing.

2. The nebulizer of claim 1, wherein the means for reducing an inhalation effort comprise a relief piston responsive to a negative pressure threshold and the means for generating an aerosol comprises a diverter, wherein the relief piston is movable independently of the diverter.

3. The nebulizer of claim 2, wherein a biasing member in contact with the relief piston determines the negative pressure threshold.

4. A nebulizer comprising:

a housing having a chamber for holding an aerosol;

an air outlet communicating with the chamber for permitting the aerosol to be withdrawn from the chamber;

an air inlet in communication with the chamber for permitting air into the chamber;

a liquid orifice in communication with the chamber;

a pressurized gas inlet adjacent the liquid orifice, the pressurized gas inlet in communication with the chamber;

a diverter movably positioned in the chamber and relative to the pressurized gas inlet and liquid orifice so as to divert pressurized gas from the pressurized gas inlet and over the liquid orifice when the diverter is in a nebulizing position; and, a valve assembly for permitting controlled amounts of air to enter into the chamber during a patient's inhalation, the valve assembly comprising:

an actuator piston connected to the diverter and positioned in the chamber, the actuator piston responsive to an initial period of inhalation through the air outlet to move the diverter into the nebulizing position; and a relief piston located in the chamber, the relief piston responsive to additional negative pressure in the chamber after the initial period of inhalation and movable to allow increased air flow into the chamber, whereby the effort necessary for a patient inhaling through the air outlet is reduced.

5. The nebulizer of claim 4 wherein the air inlet connects a supply of ambient air to the chamber.

6. The nebulizer of claim 4, wherein the valve assembly moves the diverter to a non-nebulizing position during patient exhalation.

7. The nebulizer of claim 4 further comprising a nebulizing indicator visible outside of the chamber when the diverter is in a nebulizing position.

8. The nebulizer of claim 7, wherein the nebulizing indicator is attached to the actuator piston.

9. The nebulizer of claim 8, wherein the nebulizing indicator further comprises a colored indicator flag.

10. The nebulizer of claim 4 further comprising a biasing member in contact with the valve assembly.

11. The nebulizer of claim 10, wherein the biasing member comprises a spring.

12. The nebulizer of claim 14, wherein the spring has a linear spring rate.

13. The nebulizer of claim 10, wherein the relief piston is positioned between the actuator piston and the biasing member, whereby the biasing member biases the relief piston against the actuator piston.

14. The nebulizer of claim 4, wherein the actuator piston comprises an inlet cover for movably covering the air inlet in the chamber, the inlet cover having at least one vent and connected to a coaxial shaft.

15. The nebulizer of claim 14, wherein the relief piston is positioned relative to the actuator piston and is movably responsive to an increased negative pressure in the chamber after the initial inhalation.

16. The nebulizer of claim 14, wherein the relief piston is slidably mounted on the coaxial shaft of the actuator portion.

17. The nebulizer of claim 16, wherein a biasing member holds the relief piston against the actuator piston.

18. The nebulizer of claim 17, wherein the relief piston comprises a flange portion axially aligned with the inlet cover of the actuator piston, the flange portion sized to removably cover at least one vent on the inlet cover of the actuator piston.

19. The nebulizer of claim 14, wherein the inlet cover of the actuator piston has a diameter and the diameter of the actuator piston is greater than a diameter of the relief piston.

20. The nebulizer of claim 4 further comprising a first nebulizing position wherein the diverter is a predetermined distance from the pressurized gas inlet and the relief piston forms a seal against the inlet cover of the actuator piston.

21. The nebulizer of claim 20 further comprising a second nebulizing position wherein the relief piston is spaced apart from the inlet cover of the actuator piston, whereby ambient air flows into the chamber.

* * * * *

UNITED STATES PATENT AND TRADEMARK OFFICE
CERTIFICATE OF CORRECTION

PATENT NO. : 6,450,163 B1
DATED : September 17, 2002
INVENTOR(S) : Rick Blacker et al.

It is certified that error appears in the above-identified patent and that said Letters Patent is hereby corrected as shown below:

Column 8,
Line 4, delete "outlet" and substitute -- inlet in -- in its place.
Line 14, delete "in a desired range".

Column 9,
Line 5, delete "claim 14," and substitute -- claim 11, -- in its place.

Signed and Sealed this

Twenty-second Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,450,163 B1
DATED : September 17, 2002
INVENTOR(S) : Rick Blacker et al.

It is certified that error appears in the above-identified patent and that said Letters Patent is hereby corrected as shown below:

<u>Column 8,</u>
Line 11, delete "aersol" and substitute -- aerosol -- in its place.
Line 12, delete "diveter" and substitute -- diverter -- in its place.

Signed and Sealed this

Thirtieth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,450,163 B1
DATED        : September 17, 2002
INVENTOR(S)  : Rick Blacker et al.

It is certified that error appears in the above-identified patent and that said Letters Patent is hereby corrected as shown below:

Column 8,
Line 11, delete "aersol" and substitute -- aerosol -- in its place.
Line 12, delete "diveter" and substitute -- diverter -- in its place.

Signed and Sealed this

Twenty-first Day of October, 2003

JAMES E. ROGAN
*Director of the United States Patent and Trademark Office*